(12) United States Patent
Wilson et al.

(10) Patent No.: US 8,135,179 B2
(45) Date of Patent: Mar. 13, 2012

(54) SYSTEMS, METHODS AND DEVICES FOR USE IN ASSESSING FAT AND MUSCLE DEPTH

(75) Inventors: Doyle E. Wilson, Huxley, IA (US); Viren R. Amin, Ames, IA (US)

(73) Assignee: Biotronics, Inc., Ames, IA (US)

( * ) Notice: Subject to any disclaimer, the term of this patent is extended or adjusted under 35 U.S.C. 154(b) by 344 days.

(21) Appl. No.: 12/435,735

(22) Filed: May 5, 2009

(65) Prior Publication Data

US 2009/0274340 A1    Nov. 5, 2009

Related U.S. Application Data

(60) Provisional application No. 61/050,542, filed on May 5, 2008.

(51) Int. Cl.
*G06K 9/36* (2006.01)
(52) U.S. Cl. ........................................................ 382/110
(58) Field of Classification Search ................. 382/110; 73/602, 609, 618
See application file for complete search history.

(56) References Cited

U.S. PATENT DOCUMENTS

| | | | |
|---|---|---|---|
| 4,785,817 A * | 11/1988 | Stouffer | ........................... 73/602 |
| 5,079,951 A | 1/1992 | Raymond et al. | |
| 5,194,036 A | 3/1993 | Chevalier et al. | |
| 5,208,747 A * | 5/1993 | Wilson et al. | ................. 600/443 |
| 5,303,708 A | 4/1994 | Stouffer | |
| 5,316,003 A | 5/1994 | Stouffer | |
| 5,339,815 A | 8/1994 | Liu et al. | |
| 5,353,796 A | 10/1994 | Schroeder et al. | |
| 5,452,722 A | 9/1995 | Langton | |
| 5,520,183 A | 5/1996 | Lake et al. | |
| 5,613,493 A | 3/1997 | Schafer | |
| 5,617,864 A | 4/1997 | Stouffer et al. | |
| 5,625,147 A | 4/1997 | Miles et al. | |
| 5,673,647 A | 10/1997 | Pratt | |
| 5,685,307 A | 11/1997 | Holland et al. | |
| 5,793,879 A * | 8/1998 | Benn et al. | ..................... 382/110 |
| 5,872,314 A | 2/1999 | Clinton | |
| 5,944,598 A | 8/1999 | Tong et al. | |
| 5,960,105 A | 9/1999 | Brethour | |
| 6,084,407 A | 7/2000 | Ellis | |
| 6,099,473 A | 8/2000 | Liu et al. | |
| 6,167,759 B1 | 1/2001 | Bond et al. | |

(Continued)

FOREIGN PATENT DOCUMENTS

EP    1026516 B1    4/2006

OTHER PUBLICATIONS

R.K. Johnson, E.P. Berg, R. Goodwin, J.W. Mabry, R.K. Miller, O.W. Robinson, H. Sellers, and M.D. Tokach. Evaluation of procedures to predict fat-free lean in swine carcasses. J. of Anim. Sci. 2004. 82:2428-2441.

(Continued)

*Primary Examiner* — Kara E Geisel
(74) *Attorney, Agent, or Firm* — Crawford Maunu PLLC (57) ABSTRACT

Methods, systems and devices are implemented in connection with measuring subcutaneous fat and loin depth in a portion of muscle tissue. Consistent with one such method a probe is presented to the portion of muscle tissue. The probe produces a response-provoking signal in the muscle tissue used to determine the fat and loin depth in the portion of muscle tissue.

23 Claims, 8 Drawing Sheets

U.S. PATENT DOCUMENTS

| | | | |
|---|---|---|---|
| 6,170,335 | B1 | 1/2001 | Clinton |
| 6,198,834 | B1 | 3/2001 | Benn et al. |
| 6,200,210 | B1 | 3/2001 | Pratt |
| 6,322,508 | B1 | 11/2001 | Goldenberg et al. |
| 6,591,681 | B1 * | 7/2003 | Shimada et al. ............... 73/600 |
| 6,730,034 | B1 | 5/2004 | Lang et al. |
| 7,203,911 | B2 | 4/2007 | Williams |
| 2005/0197575 | A1 * | 9/2005 | Kondoh et al. ............... 600/438 |
| 2007/0043290 | A1 * | 2/2007 | Goepp et al. ............... 600/437 |

OTHER PUBLICATIONS

Y. Liu and J.R. Stouffer. Pork carcass evaluation with an automated and computerized ultrasonic system. J. of Anim. Sci. 1995. 73:29-38.

D. Black, J. Vora, M. Hayward, and R. Marks. Measurement of subcutaneous fat thickness with high frequency pulse ultrasound: comparisons with a caliper and a radiographic technique. Clin. Phys. Physiol. Meas. 1988, vol. 9, No. 1,57-64.

National Pork Producers Council (NPPC). 2001. Pork Quality. National Pork Procedures Council, P.O. Box 10383, Des Moines, IA.

Amin V, D. Wilson, R. Roberts, and G. Rouse, "Tissue characterization for beef grading using texture analysis of ultrasonic images," Proc. of 1993 IEEE Ultrasonic Symposium, pp. 969-972, 1993.

Bondestam S, A. Alanen, and S. Toikkanen, "Correlations of liver echo intensity with cytology and chemical measurements of fat, water and protein content in live burbots (Lota Iota)," Ultrasound in Med. And Boil. 18, pp. 75-50,1992, abstract.

Haberkorn U, I. Zuna, A. Lorenz, H. Zerban, and G. Layer, "Echographic tissue characterization in diffuse parenchymal liver disease: Correlation of image structure with histology," Ultrasonic Imaging 12, pp. 155-170, 1990, abstract.

Haralick RM, K. Shanmugam and I. Dinstein, "Textural features for image classification," IEEE Trans. Sys. Man. Cyberm. 3, pp. 610-621, 1973.

Kim N, V. Amin, D. Wilson, G. Rouse, and S. Udpa, "Ultrasound image texture analysis for characterizing intramuscular fat content of live beef cattle," Ultrasonic Imaging, 20:191-205, 1998.

Layer G, I. Zuna, A. Lorenz, H. Zerban, and U. Haberkorn, "Computerized ultrasound B-scan texture analysis of experimental fatty liver disease: Influence of total lipid content and fast deposit distribution," Ultrasonic Imaging 12, pp. 171-188, 1990.

Layer G, I. Zuna, A. Lorenz, H. Zerban, and U. Haberkorn, "Computerized ultrasound B-scan texture analysis of experimental diffuse parenchymal liver disease: Correlation with histology and tissue composition," Jn. Clin. Ultrasound 19, pp. 193-201,1991, abstract.

Nicholas D, D. Nassiri, P. Garbutt, and C.R. Hill "Tissue characterization from ultrasouind B-scan data," Ultrasound in Med. And Biol. 12, pp. 135-143, 1986, abstract.

Unser M. Texture classification and segmentation using wavelet frames. 1995. IEEE Transactions on Image Processing, 4:1549-1560.

Amin V, Wilson D, Rouse G, and Zhang H. 1995. Computerized ultrasound system for on-line evaluation of intramuscular percentage fat in Longissimus dorsi muscle at a commercial packing facility. 1995 Beef Research Report, Iowa State University, Ames, Iowa.

Brondum, J. M. Egebo, C. Agerskov and H. Busk. 1998. On-line pork carcass grading with the Autofom ultrasound system. J. Anim. Sci. 1998. 76:1859-1868.

Faucitano, L., P. Huff, F.T. Teuscher, C. Gariepy and J. Wegner. 2005. Application of computer image analysis to measure pork marbling characteristics. Meat Sci. 69:537-543.

Hassen, A., D.E. Wilson, V. Amin, G. H. Rouse, and C.L. Hays. 2001. Predicting percentage of intramuscular fat using two types of real-time ultrasound equipment. J. Anim. Sci, 79:11-18.

Izquierdo, M.M., V.R. Amin, D.E. Wilson and G. H. Rouse. 1996. Models to predict intramuscular fat percentage in live beef animals using real-time ultrasound and image parameters: Report on data from 1991 to 1994. A.S. Leaflet R1324, Dept. Anim. Sci., Iowa State Univ., Ames, IA.

National Pork Board (NPB). 1999. Pork Quality Standards. National Pork Board, P.O. Box 9114, Des Moines, IA.

Newcom, D.W., T. J. Baas, and J.F. Lampe. 2002. Prediction of intramuscular fat percentage in live swine using real-time ultrasound. J. Anim. Sci. 80:3046-3052.

Morlein, D., R. Rosner, S. Brand, K.-V. Jenderka, and M. Wicke. 2004. Non-destructive estimation of the intramuscular fat content of the longissimus muscle of pigs by means of spectral analysis of ultrasound echoes. J. Meat. Sci. 69:187-199.

Schwab, C.R. and T.J. Baas. 2006. Development of a model to predict intramuscular fat in live pigs using real-time ultrasound. Iowa State University Animal Industry Report 2006, A.S. Leaflet 2050.

Silva, S.R., Afonso, J.J., Santos, V.A., Monteiro, A., Guedes, C.M., Azevedo, J.M.T., and Dias-da-Silva, A. 2006 In vivo estimation of sheep carcass composition using real-time ultrasound with two probes of 5 and 7.5 MHz and image analysis. J. Anim. Sci. 84:3433-3439.

Miller, D.C., 1998 Accuracy and Application of Real-Time Ultrasound for Evaluation of Carcass Merit in Live Animals, Department of Animal Science, NCSU.

Schinckel, A.P., Lofgren D.L., Stewart, T.S. 2000 Impact of Measurement Errors on Predicting Pork Carcass Composition: Within Sample Evaluation. Department of Animal Sciences, Purdue University.

Davis, J.K., Temple, R.S., and Mccorrmick, W.C. 1996 A Comparison of Ultrasonic Estimates of Rib-Eye Area and Fat Thickness in Cattle. J. Anim. Sci. 25:1087-1090.

Williams, A.R. 2002 Ultrasound applications in beef cattle carcass research and management. J. Anim. Sci. 80(E. Suppl. 2): E183-E-188, 2002.

Wilson, D.E. 2007 Use of Real-Time Ultrasound in % IMF Prediction for Swine. Biotronics Inc.

* cited by examiner

SYSTEMS, METHODS AND DEVICES FOR USE IN ASSESSING FAT AND MUSCLE DEPTH

RELATED DOCUMENTS

This patent document claims the benefit, under 35 U.S.C. §119(e), of U.S. Provisional Patent Application Ser. No. 61/050,542 filed on May 5, 2008, and entitled "SYSTEMS, METHODS AND DEVICES FOR USE IN ASSESSING FAT AND MUSCLE DEPTH;" this patent document and the Appendices filed in the underlying provisional application are fully incorporated herein by reference.

FEDERALLY SPONSORED RESEARCH OR DEVELOPMENT

Subject matter described in this document is based upon work supported by the Cooperative State Research, Education, and Extension Service, U.S. Department of Agriculture, under Agreement Nos. 2006-33610-16761 and 2007-33610-18441. The U.S. government has certain rights to this invention.

FIELD OF THE INVENTION

The present invention relates to systems and methods for inspecting and measuring muscle tissue parameters related to fat and lean content and quality of meat.

BACKGROUND

There are several attributes of meat quality that relate to palatability and consumer eating satisfaction. Assessments of such qualities can be useful for a variety of food animals. Such assessments can also be useful in both live animals and animal carcasses. For example, carcass weight, backfat and/or loin depth measurements may be used to determine the value of pork. Fat-free lean in swine carcasses may be predicted from fat depth and loin depth measurements.

Current fat and depth measurement processes employ manual methods, optical probes, and cross-sectional scanning, and involve highly trained technicians performing time-consuming and labor-intensive work to achieve accurate measurements. Thus, a significant challenge is presented with measuring fat and loin depths in a packing plant environment at line speeds. As an example, with many plants running their chain speed at 1200 carcasses per hour, a carcass would be measured in less than 3 seconds if the carcass is going to be measured during the packing process. In addition, pork carcasses are not routinely split anywhere along the loin that would expose the internal tissue for either a subjective or quantitative measure of fat and loin depth.

SUMMARY

The present invention is directed to systems and methods for determining quantitative measure of fat and loin depths of muscle tissue, for example, pork and beef, including from hot carcasses and live animals. These and other aspects of the present invention are exemplified in a number of illustrated implementations and applications, some of which are shown in the figures and characterized in the claims section that follows.

Consistent with an embodiment of the present invention, a method is implemented for automatically measuring fat and loin depth. An ultrasonic probe is presented to the carcass. The probe produces a response-provoking signal in the meat. A resulting signal is used to determine various tissue boundaries such as the skin-fat boundary, fat-muscle boundary, and rib-muscle boundary, so that fat and loin depth can be measured.

The above overview is not intended to describe each illustrated embodiment or every implementation of the present invention. The figures, detailed description and the appended claims more particularly exemplify these embodiments.

BRIEF DESCRIPTION OF THE DRAWINGS

The invention may be more completely understood in consideration of the detailed description of various embodiments of the invention that follows in connection with the accompanying drawings in which.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION

The present invention is believed to be useful for inspecting and measuring muscle tissue parameters, such as fat and loin depth. The muscle tissue can originate from any number of different food animals and the inspection and measuring can be obtained from live animals or animal carcasses. A specific embodiment of the present invention facilitates measurement of fat and loin depth of a pork carcass. Unless otherwise stated, the term animal references to either a live animal or an animal carcass. While the present invention is not necessarily limited to such applications, various aspects of the invention may be appreciated through a discussion of various examples using this context.

An embodiment of the present invention is directed toward a noninvasive mechanism for determining fat and loin depth of muscle tissue, such as muscle tissue from live pork or beef animals, or pork or beef carcasses. Ultrasound imaging is used to capture internal images of the muscle tissue. An image processor processes the images using algorithms specifically selected and/or tailored to use with the particular muscle tissue (e.g., the type of food animal or whether live or dead) to determine the fat and loin depth in a carcass processing line. An embodiment of the present invention can include the step of using the fat depth and muscle depth to select livestock for breeding, and rate the portion based on quality criteria, to sort livestock.

Specific embodiments of the present invention are directed toward facilitating the determination of fat and loin depth in a meat processing line. Devices, methods and systems facilitate fat and loin depth determinations at speeds and accuracy levels that are particularly useful for use on a processing line. Various aspects include, for example, streaming image capture, image selection criterion, specifically tailored algorithms and/or facilitating proper contact between the carcasses and a probe.

An embodiment of the present invention is directed toward a noninvasive system for measuring subcutaneous fat depth and muscle depth in the longissimus dorsi muscle of hot carcasses, and using such measurements to aid in determining other muscle tissue characteristics, such as percentage intramuscular fat (IMF). The measurements are made real-time, for example, on carcasses that are moving on a transport rail at a nearly constant rate of 1,200 carcasses per hour. Measurements are made from live video-streaming ultrasound images as the carcasses move past a scanning station. The scanning station can be fully automated, manual or a combination thereof.

System output data is interfaced with the packing plant individual carcass identification system and hot carcass weighing scale. The combined data is used by the plant to determine individual carcass value and can be useful for differentiating and sorting of each carcass for alternative fabrication and processing of wholesale pork products within minutes after harvest.

Figure 1:
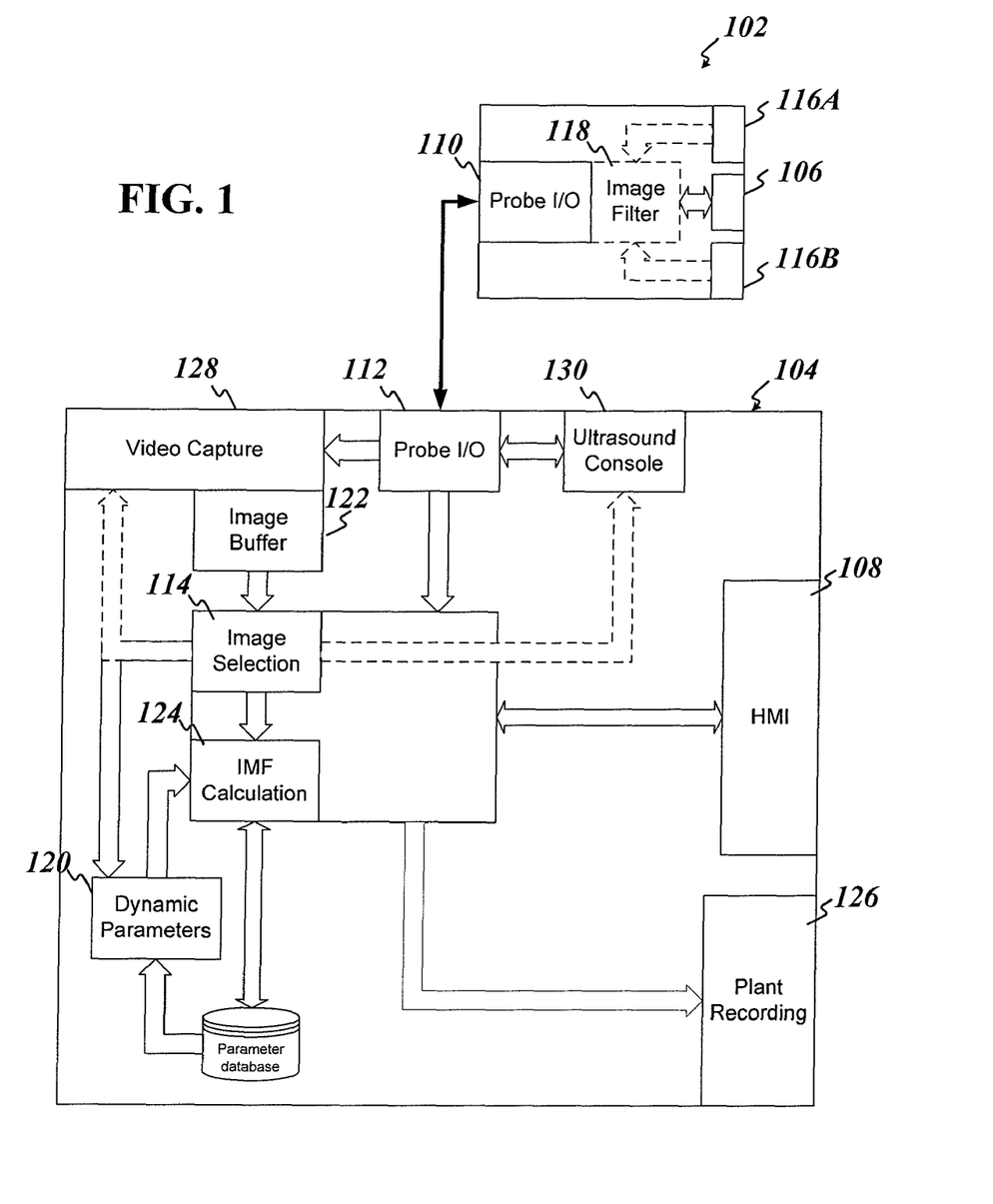
FIG. 1 shows a system-level diagram, consistent with an example embodiment of the present invention.

By way of example, FIG. 1 illustrates a system for use in inspecting and measuring muscle tissue parameters in carcasses, according to a specific embodiment of the present invention. Probe 102 communicatively connects to processing block 104 using probe input/output (I/O) 110, 112. This connection can be implemented using, for example, a wired connection, wireless connections or a removable storage medium. Wired connections can be implemented using any suitable (e.g., bandwidth and reliability) protocol including, but not limited to, universal serial bus (USB), IEEE 1394 and Ethernet. In a specific instance, the probe is connected using a data-carrying cable (e.g., electrical or optical). In another instance, the probe is integrated into a single device that includes the processing block 104. Wired connections can also be implemented using a more temporary connection, such as a removable data storage device or a cradle for placement of the probe. Wireless connections for non-ultrasound communications can be implemented using an assortment of different techniques and protocols including, but not limited to, 802.11x or ultra-wideband (UMB).

Probe 102 provides images of the carcass using ultrasound imaging. An ultrasound transducer 106 converts control data into transmitted sound and received sound into image data. In a specific example, the transducer is a piezoelectric transducer that converts between electrical and physical vibration energy. Embodiments of the invention are designed to allow use of a variety of existing or future imaging techniques (e.g., other than piezoelectric transducers). The actuation of such transducers can be controlled by ultrasound controller 130. For example, controller 130 can provide a stimulus profile for capturing a series of images from the same carcass.

Embodiments of the invention include a human-machine interface (HMI) 108. HMI 108 facilitates operation, monitoring or otherwise interfacing with the system by a human operator.

Image selection block 114 is an optional component that selects between a set of images obtained from the probe 102. Image selection block may facilitate the selection of images based on direct or secondary indicia of image quality or usability. For example, acquired images may be screened for blurriness, the existence or absence of certain features, the existence or absence of one or more subset regions of interest (ROI) within the image, and for conditions under which the images were acquired.

With respect to image acquisition conditions, it has been observed that the quality of ultrasonic images acquired from animal carcasses can be affected by the pressure applied between the probe transducer and the carcass. Thus, in reference to FIG. 1, the probe 102 optionally includes one or more pressure sensors such as load cells 116A and 116B. Information from the pressure sensors may be used by an optional image filter 118 within the probe 102 to decide whether to capture and transmit images to the processing block 104. In other embodiments, the pressure data is transmitted to the processing block 104 for analysis, at which point the images may be recorded using video capture 128 and/or buffer 122 and retained for further analysis or discarded based on the pressure readings. In another example, the processing block 104 analyzes the pressure data and in response determines whether or not to activate the ultrasound transducer. Feedback signals may be provided to control further image acquisition by the probe and/or to provide an operation status indication (e.g., yellow light for non-acquisition stand-by mode when the probe is not applied or insufficient pressure is applied, red light for non-acquisition based on too much pressure or unbalanced pressure, and green light for ultrasonic activation and image acquisition due to proper application of the probe).

During image selection screening, images are removed or discarded if the quality and/or pressure criteria are not met. In certain embodiments, images discarded based on such screening may be stored for later analysis, for example, to facilitate system diagnostics, for adjusting of screening algorithm parameters, and so forth.

According to specific embodiments of the present invention, processing parameters 120 used by the algorithms for determining muscle tissue characteristics can be dynamically adjusted for each carcass. For example, each carcass has a specific makeup with regards to the tissue depths of various tissue types. These differences can affect the captured image data as, for example, different tissue types can exhibit different sound propagation properties. Tissue types that can be monitored for dynamic adjustments include, but are not limited to, subcutaneous fat, muscle (loin), skin and bones. In a specific instance, the subcutaneous fat depth and loin depth within a region of interest are determined. These determined depths may then be used as further parameters in algorithms for determining other muscle tissue characteristics, such as IMF.

Ultrasound device calibration can be particularly useful for maintaining consistency between measurements where, for example, components of the device are replaced or operation parameters change (e.g., changes over time due to use or due to temperature variations). One mechanism for calibration involves the use of a default device that is already calibrated. Measurements are taken for each device and the parameters for the device under calibration are modified so that the results coincide with the results of the default device. Another mechanism involves the use of a known item from which fat and loin depth measurements are taken. The item could be one or more carcasses.

Figure 2:
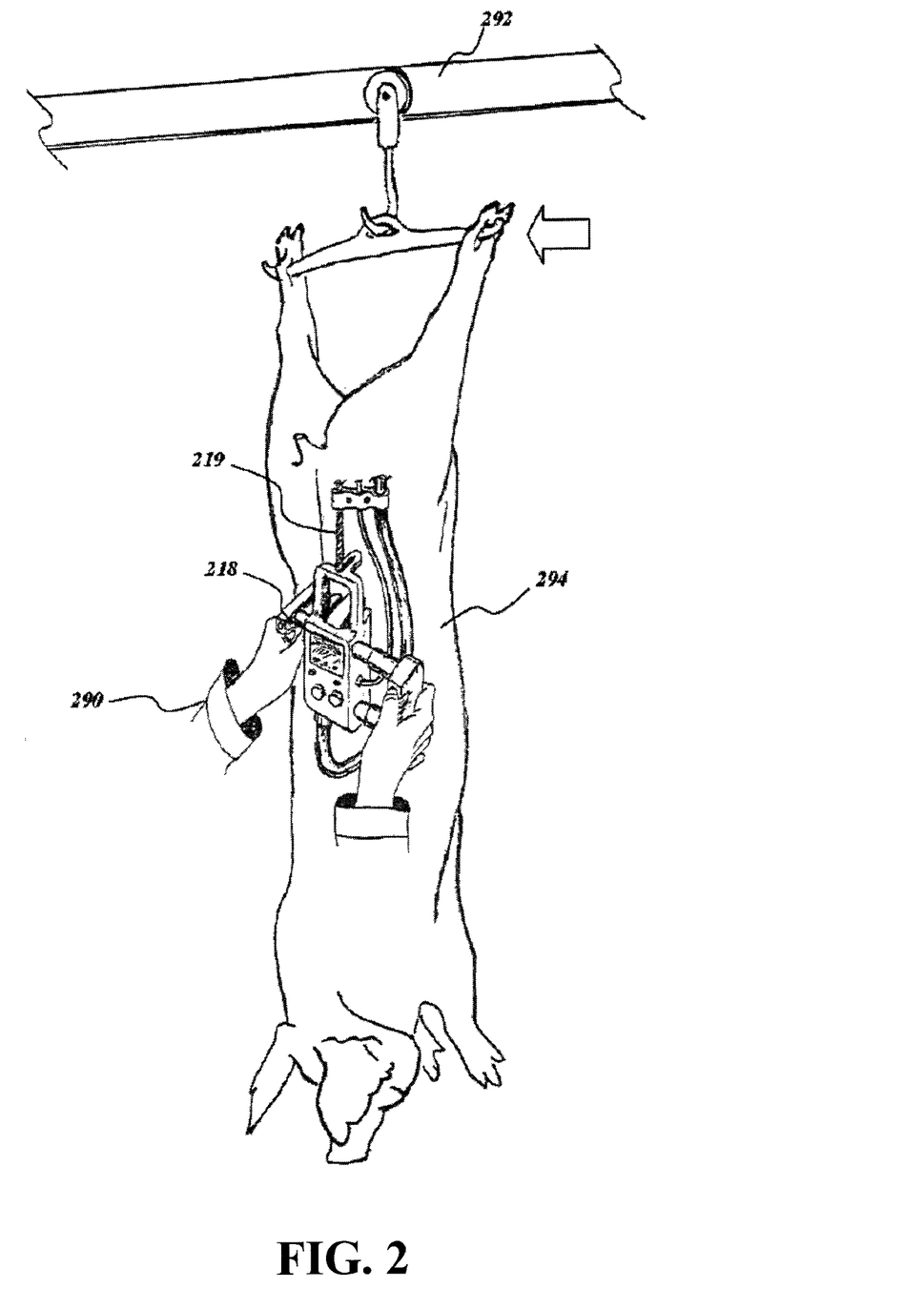
FIG. 2 illustrates ultrasonic scanning of a hot carcass within a packing plant environment, consistent with an example embodiment of the present invention.

By way of example, FIG. 2 illustrates a meat packing plant environment where hot carcasses, such as carcass 294, are conveyed along an overhead conveyor system 292 in a direction indicated by the arrow. As the carcasses pass an operator measurement position, an operator 290 applies an ultrasonic transducer probe from ultrasound system 218 to a specified portion of the carcass 294. Images acquired from the ultrasound system 218 are provided via connection 219 to a data acquisition system for data analysis.

Ultrasound video capturing and processing at a faster frame rate may be used advantageously for automated processing as well as certain applications such as chute-side analysis and carcass evaluation at a faster line speed (e.g., 1200 carcasses per hour). In accordance with certain embodiments, systems and methods of the present invention are used to capture and process ultrasound video imagery at variable frame rates (e.g., from 1 frame per second (fps) to 60 fps). Various processing modules or sets of processing modules can be selected and applied to the series of captured frames to extract tissue characteristics and attributes. Possible processing algorithms include frame editing, automatic image quality detection, fat thickness and muscle depth evaluation, and image texture processing.

In exemplary embodiments, the present invention may be used to first screen the acquired images for sufficient image quality. Next, image processing algorithms may be applied to automatically determine the fat layer boundaries, and then determine the rib locations (if visible on the image) and the top and bottom edges of the intercostales muscles. In an extension of the present invention, the fat and loin depth measurements may be used to locate one or more regions of interest of an image frame for further analysis, and selects and applies one or more image processing techniques in sequence or in parallel to the determined ROI for prediction of other muscle tissue attributes such as IMF.

Video frames are continuously captured, and processing of the captured images is implemented in response to the sensors on the transducer fixture indicating that a correct carcass skin to transducer lens face pressure range has been achieved. The pressure can be continuously monitored. Each frame for which a corresponding pressure measurement meets the pressure range criteria is evaluated for ultrasound penetration level through the first designated amount of skin (e.g., 0.69 mm for pork) as determined by histogram thresholding along the length of the probe lens. Segments of the frame at the designated depth that exceed a set reflection intensity level (e.g., 179 pixel grey scale) are gated, and regions below these segments can be excluded from the development of texture parameters. Segments of the frame at the designated depth that exceed a set reflection intensity level (e.g., 200 pixel grey scale) are gated, and any region below these segments can be excluded from a determination of subcutaneous fat depth and muscle depth. Blurred frames as detected by a wavelet transformation algorithm may be excluded from further processing of tissue texture, but may be used for subcutaneous fat depth and muscle depth.

Frame editing procedures may optionally include frequent monitoring of the image contrast level by processing the grey scale bar on the ultrasound image, and monitoring for significant electromagnetic interference corrupting image frames. According to a specific embodiment of the present invention, the fat depth and loin depth of a swine carcass is determined. Fat depth and loin depth measurements are used in estimating fat free lean content in live and carcass food animals. Fat and loin depth measurements using ultrasound images offer a non-invasive method for this procedure. Automation of these depth measurements from ultrasound images can provide fast, efficient and consistent measurements compared to visual and manual tracing. Automation of depth measurements includes the automatic determination of the boundary positions for fat top, fat bottom, rib top, and the top and bottom interfaces of the intercostales muscles. These interfaces can be measured between all the rib pairs in longitudinal ultrasound images of live animals or carcass data (e.g., in swine, positioned between the $10^{th}$ and $13^{th}$ ribs). This offers the user the flexibility to select the preferred location for depth measurements. The following relationships can be defined:

Fat depth=Fat Bottom boundary−Fat top boundary

Loin depth=Rib top boundary−Fat bottom boundary, or

Loin depth=Intercostales muscles boundary−Fat bottom boundary.

The automation algorithm includes three subsections, each determining one of the above-mentioned boundary positions. Ultrasound image size (number of pixels along rows and columns) can vary depending on ultrasound scanner and frame grabber used for image capturing, and so the algorithm may be independent of image pixel size. The fat depth and muscle depth estimates are adjusted for the differences in ultrasound velocity in fat and muscle, respectively.

Ultrasound calibration software algorithms may be used to set image capturing parameters to a given reference. Calibration works in combination with an ultrasound scanning device, the analog video signal from the scanner, and an image frame grabber. Calibration software may be used to automatically determine if the source of the video comes from any ultrasound equipment types used in livestock scanning. Based on analysis of grey scale bars present in the images from these machines, calibration determines actual signal voltage level and compares with a 1 volt reference.

In exemplary embodiments, the present invention may be implemented as an online fat and loin depth measurement, for example, usable by a packing plant to sort pork carcasses for processing, product marketing, and paying pork producers for their harvested pigs. Systems and methods of the present invention may be employed on hot pork or beef carcasses (hot, meaning within 45 minutes postmortem), and where skin, fat, and muscle boundary determination is desired to be performed real-time so that the data can be interfaced directly with other carcass data and before the carcass leaves the hot carcass processing part in the harvesting plant.

In systems and methods of the present invention, an operator (human, automated, or combination) positions the ultrasonic probe on the skin of the carcass, and the remaining processes follow automatically, including the capture of carcass identification and live video image frames. In exemplary pork loin processing embodiments, the operator positions and maintains the ultrasound transducer (probe) fixture so that the probe is vertically aligned with and parallel to the spine or midline of the carcass, between 2 and 7 cm lateral to the midline, and on either side of the carcass. In typical packing plant environments, the carcass is vertically suspended on a trolley system. The top portion of the transducer face may be positioned so that the ultrasound image will include the last 3 to 4 ribs of the carcass.

Figure 3:
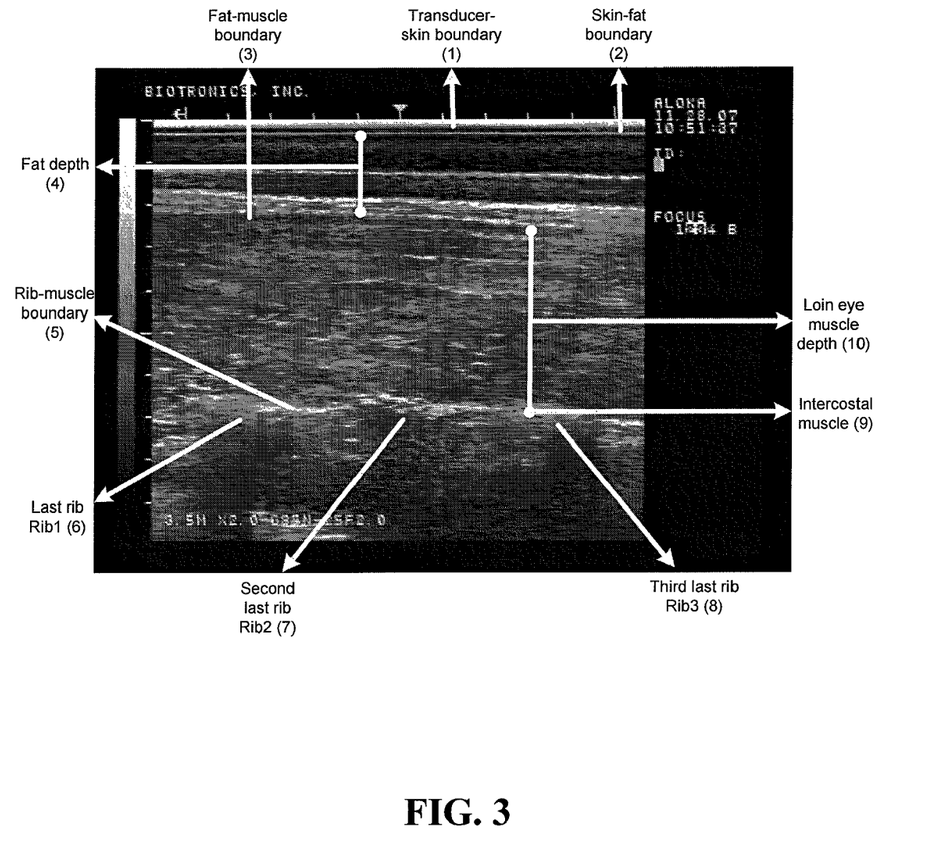
FIG. 3 is an ultrasound image of a swine carcass loin eye muscle for determination of fat and loin depth, consistent with an example embodiment of the present invention.

FIG. 3 is an ultrasound image of a swine carcass loineye muscle, captured using an Aloka SSD 500V ultrasound scanner, a 12.5 cm linear transducer of 3.5 MHz and a Sensoray 2255S frame grabber. It is a longitudinal image of a swine carcass positioned over the last 3 to 4 ribs. The top-most light-grey band is the transducer skin boundary 1. Below this is a very thin light grey line which is the skin-fat boundary 2. There are further light-grey bands that correspond to three fat layers and fat-muscle layer boundary 3. The last three ribs, ribs 6, 7, and 8, respectively, are clearly seen in the lower half of the image as three vertical columns with the intercostales muscles 9 holding the ribs. The muscle above these ribs is the longissimus dorsi muscle. The boundary between the loin eye muscle and the ribs is the rib-muscle boundary 5.

A process for determining the fat depth 4 and loin eye muscle depth 10 may be automated for swine carcass data in a real time live-streaming scanning system. The fat depth 4 is the difference between the two boundary positions, skin-fat 2 and fat-muscle 3; whereas, the loin eye muscle depth 10 is the difference between the two boundary positions, fat-muscle boundary 3 and rib-muscle boundary 5. Exemplary automation algorithms for fat and loin depth are discussed in detail in the following discussions. The percentage of fat-free lean in pork muscle tissue is calculated using the fat depth and loin eye muscle depth as also discussed below.

Figure 4A:
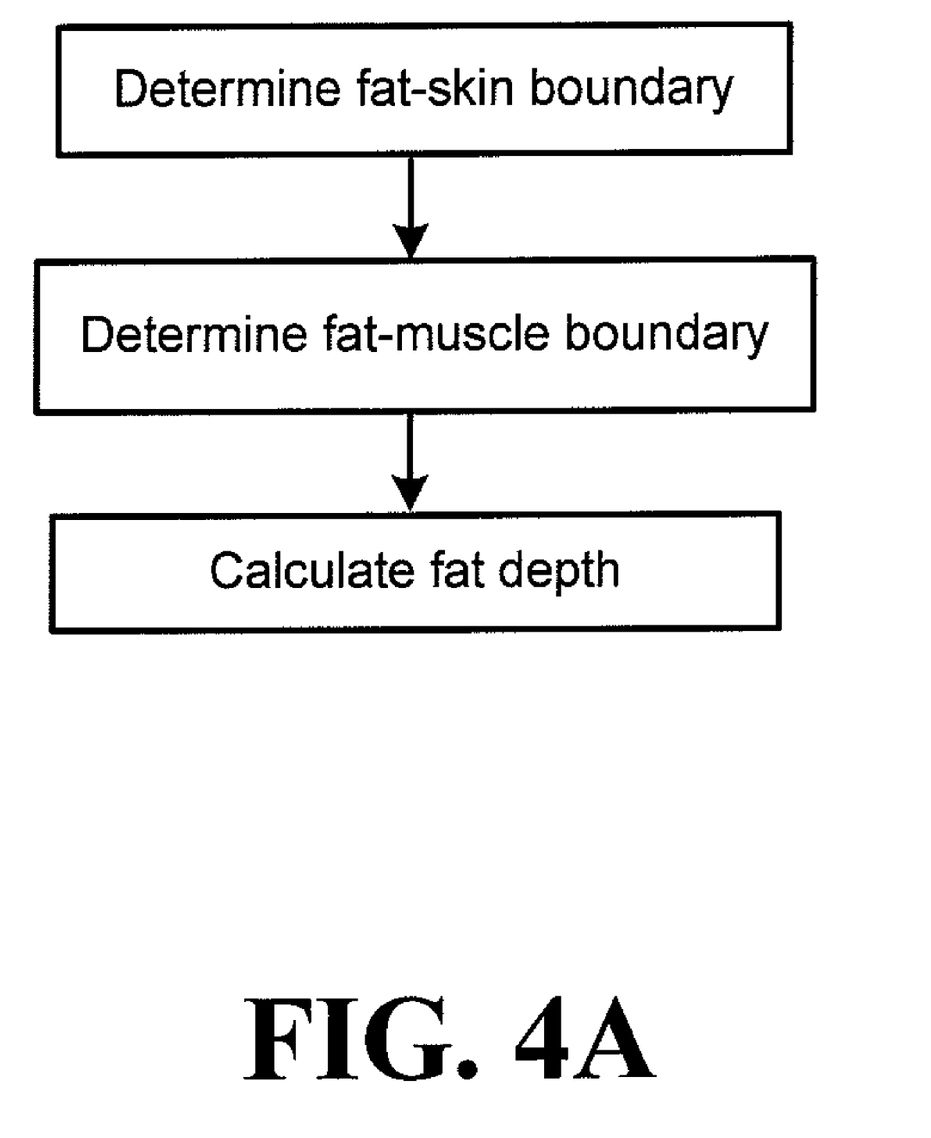
FIG. 4A shows a block diagram of an example fat depth automation algorithm, consistent with an example embodiment of the present invention.

Fat depth automation algorithms in accordance with certain embodiments include determining the two boundary positions, skin-fat and fat-muscle, from the ultrasound image of a swine carcass. FIG. 4A shows a block diagram of an example fat depth automation algorithm, which includes determining the fat-skin boundary, determining the fat-muscle boundary, and calculating the fat depth.

Figure 5:
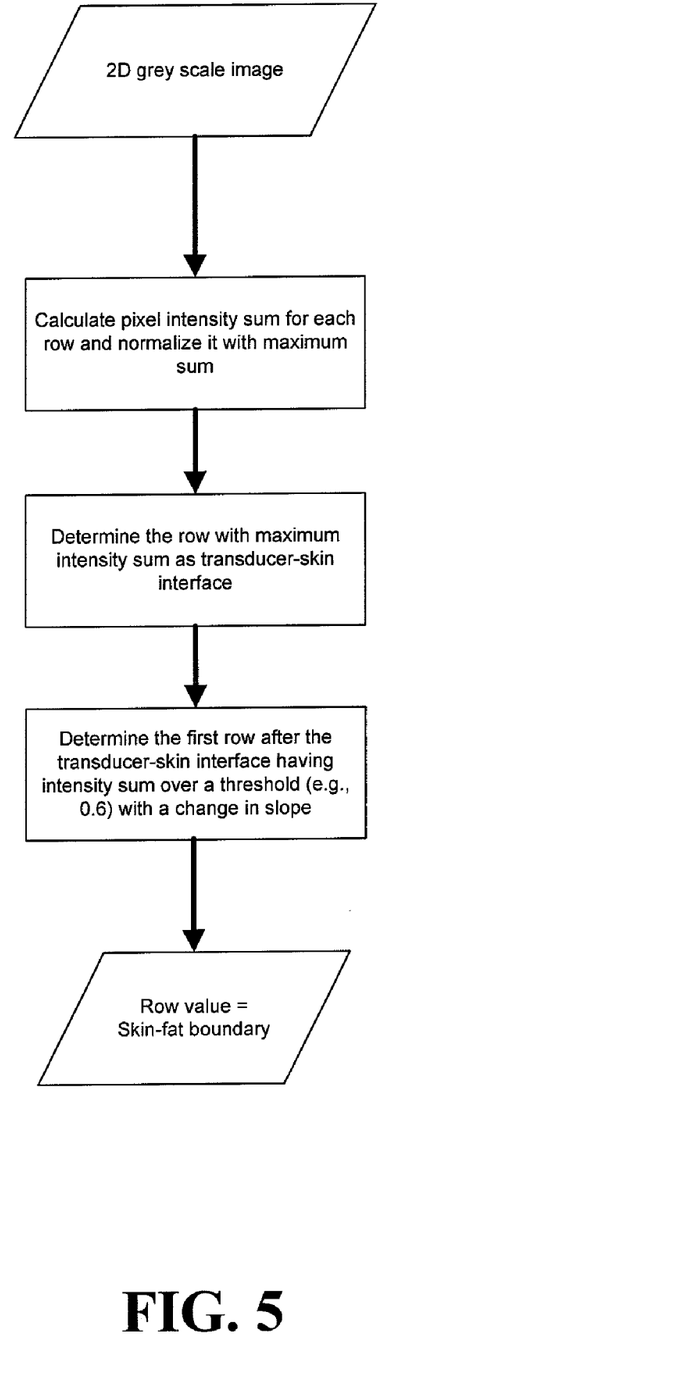
FIG. 5 shows a block diagram of an example skin-fat boundary automation algorithm, consistent with an example embodiment of the present invention.

FIG. 5 shows a block diagram of an example skin-fat boundary automation algorithm, consistent with an example embodiment of the present invention. Threshold-based operations are used on the captured ultrasound image based on the horizontal resolution of grey level intensity to determine the desired boundary positions. From a two-dimensional (2D) grey scale image, a processing circuit calculates pixel intensity sum for each row and normalize it with a maximum sum. For instance, the sum of grey level intensity along each row (horizontal resolution) and the entire image width (typically 640 pixels) is calculated. The sum is normalized with respect to the maximum of sum value. The processing circuit then determines the row with maximum intensity sum and identifies it as the transducer-skin boundary. The intensity sum can be scanned after a set number of pixel rows (e.g., 10) from the transducer-skin boundary until the end of the rows for the skin-fat boundary. The next step involves identification of the first row after the transducer-skin interface having intensity sum over a threshold (e.g., 0.6) with a change in slope. This row value is set to be the skin-fat boundary.

Figure 6:
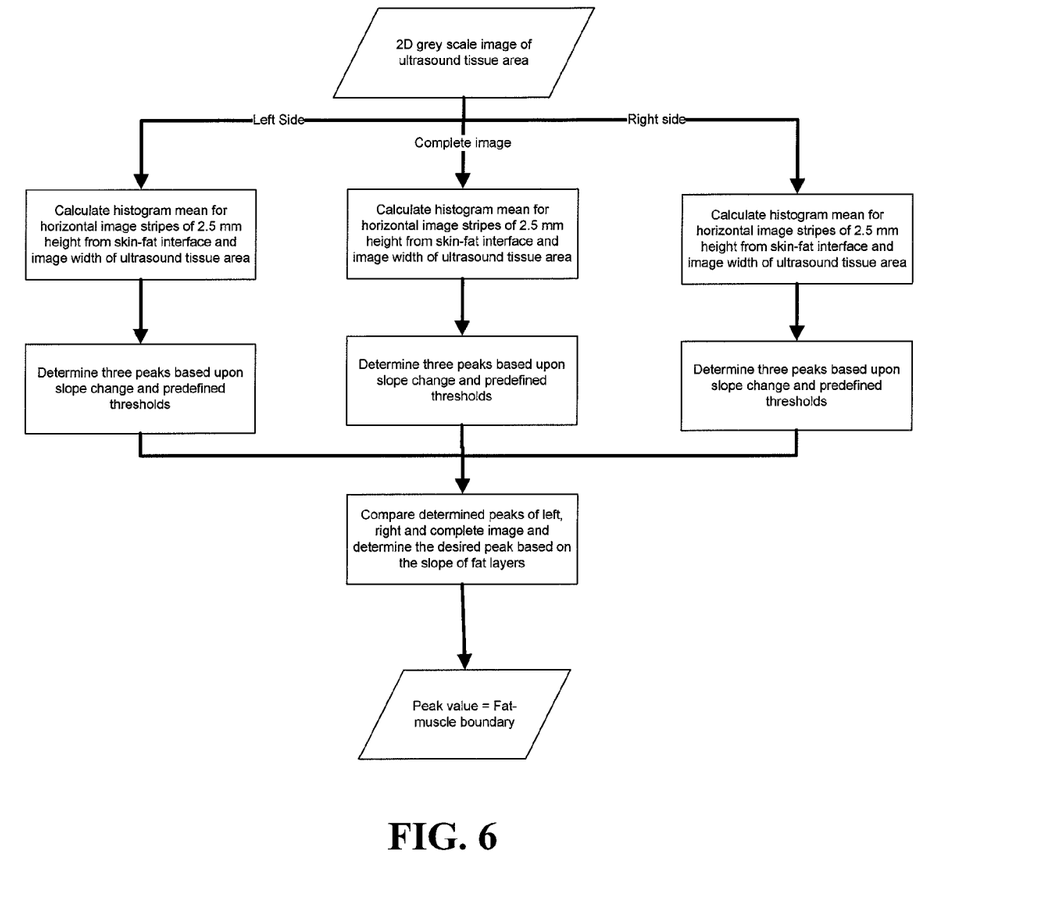
FIG. 6 shows a block diagram of an example fat-muscle boundary automation algorithm, consistent with an example embodiment of the present invention.

FIG. 6 shows a block diagram of an example fat-muscle boundary automation algorithm, consistent with an example embodiment of the present invention. A 2D grey scale image (e.g., from of ultrasound imaging of the desired tissue area) is input to a processing circuit. The processing circuit performs multiple processing steps on different portions of the image. FIG. 6 shows one example embodiment where the processing circuit performs the processing steps on the complete image as well as left and right (subset) portions of the image. This division into three different sections is but one example. The processing circuit could perform the steps on more or less image sections by partitioning the image in a different manner. For each partition, the processing circuit calculates histogram mean for horizontal image stripes of a certain depth (e.g., 2.5 mm height) from skin-fat interface and image width that is the same as that of the ultrasound tissue area. Three peaks are identified using slope change and predefined thresholds. A comparison is performed for the determined peaks of different partitions (e.g., left, right and complete image partitions). The desired peak is then determined based on the slope of fat layers. This peak value can then be used as the fat-muscle boundary.

Figure 7:
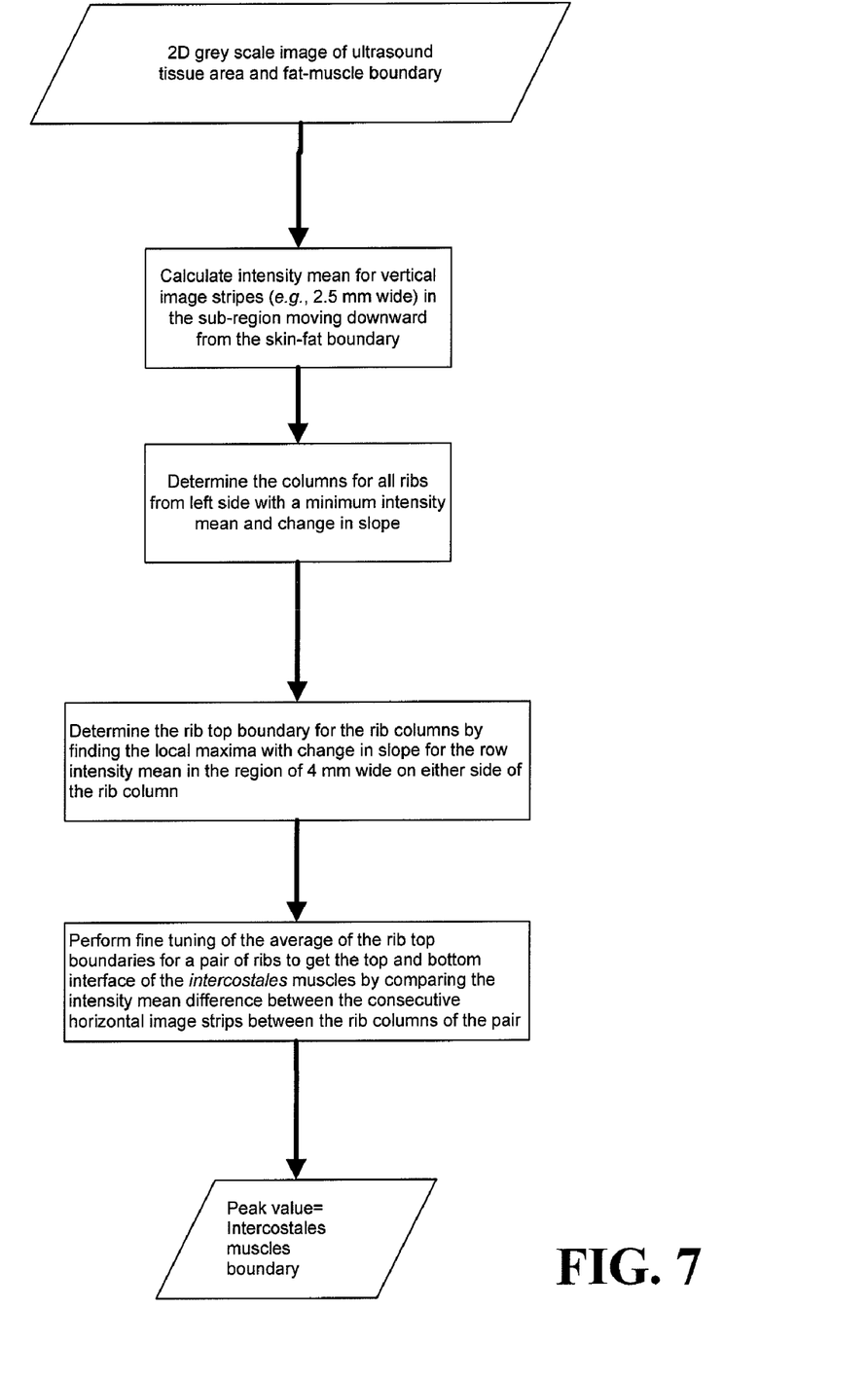
FIG. 7 shows a block diagram of an example intercostales muscles boundary automation algorithm, consistent with an example embodiment of the present invention.

FIG. 7 shows a block diagram of an example intercostales muscles boundary automation algorithm, consistent with an example embodiment of the present invention. A processing circuit uses a 2D grey scale image of the ultrasound tissue area. The portion of the image used in this processing can be defined as the region vertically downwards from a determined fat-muscle boundary (e.g., from the automation algorithm of FIG. 6) and using a width that is the same as that of the ultrasound tissue area. The processing circuit calculates an intensity mean for vertical image stripes of a certain width and depth (e.g., 2.5 mm wide and from 5 mm deep) in the subregion selected. Columns are determined for all the ribs from the left side with a minimum intensity mean and change in slope. The processing circuit determines the rib top boundary rows for the rib columns by finding the local maxima with change in slope for the row intensity mean in the region 4 mm wide on either side of the rib column. Fine tuning of the average of the rib top boundaries is implemented for a pair of ribs by comparing the intensity mean difference between consecutive horizontal image stripes between the two rib columns. The strip determined is used to define the top or bottom of the intercostales muscles boundary.

An image intensity histogram mean may be computed for sliding image strips of a predefined height (e.g., 13 pixels) and width that is the same as the actual tissue area (e.g., 500 pixels), for example, moving across the rows from the skin-fat boundary to bottom with a step size equal to half the strip height (e.g., 6 pixels). The starting row of each sliding image strip and its corresponding histogram mean are stored in an array. The strips corresponding to approximately 30 mm region (e.g., strips 1 to 25) covering the upper half of an image are processed further and the strip having a local maximum greater than a specific threshold (e.g., 0.8), and with a change in slope, is determined. As such, the selected strip should have the highest histogram mean greater than the threshold in this region, and this value should be higher than its consecutive previous and next strips. All the possible strips (1/2/3) corresponding to the three fat layers, satisfying the predefined threshold and change of slope criteria, are determined and combined in a group. The starting row of the last strip in this group corresponding to the third fat layer is assigned as the average row position for the fat-muscle boundary position. Fine adjustments are performed on this boundary position to get the closest fat-muscle boundary in the region between different pairs of ribs, at the same location as that of the loin depth measurements.

The fat depth may then be calculated as the difference between the two boundaries corresponding to skin-fat and fat-muscle. This difference is divided by a pixel to mm conversion ratio (e.g., 1 mm to 3.94 pixels) for the given equipment setup. There is also a difference in ultrasound velocities for the fat (e.g., 1430 m/s) and the scanner (e.g., 1540 m/s), and thus an adjustment factor may also be applied by multiplying the ratio of the velocities (e.g., 0.92857) by the calculated depth. For the values given above, the final fat depth formula is:

$$\text{Fat depth} = ((\text{Fat-muscle boundary row} - \text{Skin-fat boundary row})/3.94) * 0.92857$$

Figure 4B:
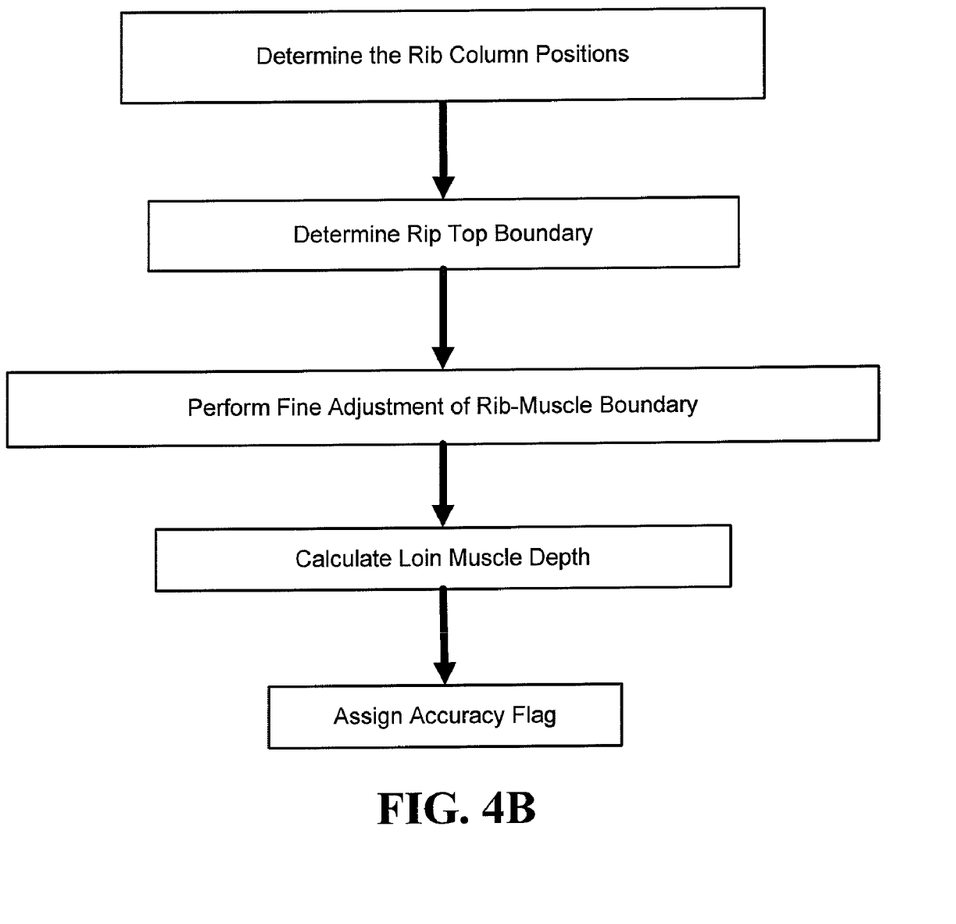
FIG. 4B shows a block diagram of an example loin depth automation algorithm, consistent with an example embodiment of the present invention.

An example algorithm for loin depth measurement proceeds as illustrated in the block diagram in FIG. 4B. First, the rib column positions for the first three ribs (labeled 6, 7, and 8 in FIG. 3) starting from the left side of the image are determined. Secondly, the rib top boundaries corresponding to these rib columns are calculated. Then, these rib top boundaries are processed for fine adjustment to determine the boundary of the intercostales muscles. Finally, the loin eye muscle depth is calculated using the difference between the fat-muscle and the rib-muscle boundaries and proper pixel to mm conversion ratio for the particular study setup. The depth value is adjusted for a correction factor for ultrasound velocity in muscle tissue. An accuracy flag may be assigned to each depth measurement based on the image characteristics encountered in the algorithm to get the confidence level for the measurement. Each of these steps is discussed in detail below.

Accordingly, one embodiment of the present invention relates to determining the skin-fat boundary, the fat-muscle boundary, and the intercostales muscles interface. The method involves capturing an image data from a response-provoking signal, such as an ultrasound signal. The captured image is analyzed by applying (user-defined) depth settings for preferred interface locations for fat and loin depth measurements. For example, the analysis can include the steps of a) selecting one pair of ribs for depth measurement, b) selecting multiple pairs of ribs and averaging the depth across the selected multiple ribs, and c) selecting the top or bottom interface of the intercostales muscles for loin depth.

A filtering function is applied to identify the dark vertical regions in the captured image, which can be caused by very high acoustic impedance at the skin. This can be particularly useful for compensating for dark regions that are the result of excessive scalding or burner singeing. These dark regions are then restricted from further image processing. The top interface for fat depth is the skin-fat boundary and is determined by comparing the normalized intensity sum (computed for each row across all the columns) with a predefined threshold and a change in slope criteria. The interfaces corresponding to the fat layers in the captured images are determined by comparing the grey level intensity histogram mean of selected moving horizontal image stripes with a predefined threshold. The interface for the bottommost fat layer is defined as the fat-muscle boundary. This represents the bottom interface for fat depth and the top interface for loin depth measurement.

The rib shadow column locations are identified by comparing the intensity average values calculated for vertical slices moving across the width of the image below the fat-muscle boundary. The rib top boundaries are determined by comparing the intensity average values for small horizontal slices across the each identified rib column. The bottom interface is used to determine loin depth. Depending upon (user-defined) settings, this interface can be the either top interface or the bottom interface of the intercostales muscles. This interface is determined by computing the intensity average differences for a pair of consecutive horizontal stripes starting from the average rib top boundary up to the bottom-most row of the image and between the two rib columns. The pair of strips with the lowest negative difference is identified. The first strip in this pair of strips is defined as the top interface of the intercostales muscles. The pair of strips with the highest positive difference is identified. The first strip in this pair is defined as the bottom interface of the intercostales muscles.

The results of these steps can be used for calculating the fat depth and loin depth. For example, the fat depth can be computed as a distance between the skin-fat boundary and fat-muscle boundary. The loin depth can be computed as a distance between the fat-muscle boundary and intercostales muscles boundary (e.g., top or bottom interface of intercostales muscles). A pixel scaling factor can then be applied (e.g., pixel to mm or pixel to inches) for the given system setup to determine the actual fat depth and loin depth. Moreover, a velocity correction factor can also be applied to the fat depth or loin depth to compensate for the effect of different ultrasound velocities in fat and muscle tissue.

The fat and muscle tissue of swine carcass indicated in an ultrasound image takes up only a portion of the image area (e.g., from rows 49 to 448 and columns 53 to 502 in a 640×480 pixel image). In a given image, a sub-image may be selected and considered for determining rib column positions for all the ribs from the left side of the image. Small sliding vertical strips (e.g., 10 pixels wide) are selected in the sub-image. The grey level intensity average is computed for each sliding strip. The starting column of each sliding strip and its corresponding intensity average is stored in an array. The array length is equal to the number of sliding strips in the sub-image.

The computed intensity average for sliding strips across columns is used to determine the rib column positions for the ribs starting from the left side of the image. The main focus to measure the loin depth is between a pair of ribs due to the preferable position of image ROI for texture analysis for the prediction of IMF in the same region. There are some exceptions to this where the image may be dark in this region (e.g., due to burning of the skin).

A group of strips starting from the left side of the image (e.g., the first 8 strips) from the column intensity average array are considered to determine the first rib column position. The strip having local minima of the intensity average with a change in slope is determined. The selected strip should have the lowest intensity average in this range, and its value should be lower than its consecutive previous and next strips. The starting column of this selected strip is assigned as the column position for the first rib. If the desired strip is not found, the first rib column position is assigned to zero. Since the two rib columns are not closer than approximately 100 pixels (e.g., 25 mm), the previous rib range is advanced by a predefined interval (e.g., 8 strips) and used as the range for the next rib. A similar procedure is performed to find a strip having local minima of the intensity average with a change in slope to determine the next rib column position. If the desired strip is not found, the rib column position is assigned to zero. This procedure is repeated to get all the possible rib column positions starting from the left side of the image.

After determining the first and second rib positions, the row corresponding to the rib top boundary for these two ribs is determined in the next step. Based on the possibilities of both the rib columns being zero or non-zero, there are 4 cases for calculating rib top boundary rows (refer to FIG. 3 for examples of Rib1 and Rib2 positions):

i) Rib1≠0 andRib2≠0;
ii) Rib1=0 and Rib2≠0;
iii) Rib1≠0 and Rib2=0; and
iv) Rib1=0 and Rib2=0.

In case (i), the rib top boundary is calculated for the two rib columns using the process described in detail below. The average of the two rib top boundary rows is calculated and the algorithm proceeds to the next step in order to perform some fine adjustments to get the closest rib-muscle boundary required for measurement of the loin eye muscle depth.

In cases (ii) and (iii), the rib top boundary for the non-zero rib value is calculated and the algorithm proceeds to the next step of fine adjustment.

In case (iv), the final rib-muscle boundary and loin eye muscle depth are both assigned to zero and an accuracy flag is set to indicate incorrect measurement and exit from the algorithm.

For every non-zero rib column 1 or 2, a sub-image is selected defined by the row starting from the fat-muscle boundary plus a set number of pixels, such as 120, to a set final row, such as row 420 (in mm conversion, fat-muscle boundary plus 30 mm to 105 mm). Within this sub-image a small moving image box of a set number of pixels (e.g., 13) high is selected starting from the bottom-most row. The width of this box is a set number of pixels (e.g., 30) covering the area in the vicinity of the respective rib column. The grey level intensity average of this image box is calculated. The image box is moved upwards along the rows with a step size of a set number of pixels e.g., 6) and the intensity average is computed for all the image boxes in this sub-image. The starting row of each image box and its corresponding intensity average values are stored in an array. The box having local maxima of the intensity average with a change in slope is determined for the respective rib column. The starting row of this selected box is assigned to the rib top boundary position for the respective rib. If the desired box is not found, the rib top boundary position is assigned to the starting row of the local maxima irrespective of change in slope criteria. This procedure is performed for all non-zero rib column positions to determine respective rib top boundary positions.

In the next step, fine adjustments may be performed on the rib top boundary rows to obtain the closest row position near the rib-muscle boundary for the loin eye muscle depth. For example, the intercostales muscles area between the ribs is processed to get the closest point of the rib-muscle boundary. First, the average of rib top boundary rows for non-zero rib columns is computed. There are three possible cases for column range to perform fine adjustment based on rib column values with the step equal to a set number of pixels (e.g., 15) as below:

i) If (Rib1≠10 and Rib2≠0), then the column range is from (Rib1−step) to (Rib2+step).
ii) If (Rib1≠0 and Rib2=0), then the column range is from (Rib1−step) to (Rib 1+step).
iii) If (Rib1=0 and Rib2≠0), then the column range is from (Rib2−step) to (Rib2+step).

Once the column range is decided, the row range for fine adjustment is selected to the region with row position starting from average rib top boundary minus a set number of pixels (e.g., 35) to average rib position plus a set number of pixels (e.g., 30) which is around 8 mm up and down from the average rib top boundary. Then, starting from the top row, a small image strip (e.g., 8 pixels height and width equal to the column range) is considered and its average grey level intensity is computed. The strip is moved down (e.g., using a 4 pixel step size) until the bottom row is reached, and the same computation is performed for all the strips. The starting row of each image strip and its corresponding intensity average values are stored in an array. The difference between the intensity average values for each strip with its next consecutive strip is calculated. The starting row of the strip with the lowest negative difference is assigned to the final rib-muscle boundary row position required for the loin eye muscle depth measurement. If the desired strip is not found, the final rib-muscle boundary is assigned to the average rib-top boundary. This boundary corresponds to the top interface of the intercostales muscles.

To determine the bottom interface of the intercostales muscles, the row range is selected as the region with row position starting from the rib-muscle boundary plus a set number of pixels (e.g., 24) to the rib-muscle boundary plus a set number of pixels (e.g., 70) which is approximately 18 mm down from the rib-muscle boundary. The column range is the same as the one used for fine adjustment of the rib-muscle boundary. Then, starting from the top row, a small image strip (e.g., height of 13 pixels and width equal to the column range), is considered, and its average grey level intensity is computed. The strip is moved down (e.g. using a 6 pixels step size) until the bottom row is reached, and the same computation is performed for all the strips. The starting row of each image strip and its corresponding intensity average values are stored in an array. The strip having local maxima of the intensity average with a change in slope is determined. The starting row of this selected strip is assigned to the bottom interface of the intercostales muscles. If the desired strip is not found, this boundary position is assigned to the starting row of the local maxima irrespective of the change in slope criteria. The user has the flexibility to measure the loin depth at a preferred location with respect to the intercostales muscles and the ribs. For example, one can measure loin depth up to the rib-muscle boundary (top interface of the intercostales muscles) or to the bottom interface of the intercostales muscles between any of the rib pairs.

For fine adjustment of the fat-muscle boundary, the row range for fine adjustment is selected as the region with row position starting from the average fat-muscle boundary minus a set number of pixels (e.g., 24) to the average fat boundary plus a set number of pixels (e.g., 24). This is around 6 mm up and down from the average fat-muscle boundary. The column range is the same as the one used for fine adjustment of the rib-muscle boundary. Then, starting from the top row, a small image strip (e.g., 13 pixels height and width equal to the column range), is considered, and its average grey level histogram mean is computed. The strip is moved down (e.g., using a 6 pixel step size) until the bottom row is reached, and the same computation is performed for all the strips. The starting row of each image strip and its corresponding histogram mean values are stored in an array. The difference in histogram mean values for each strip with its next consecutive strip is calculated. The starting row of the strip with the highest positive difference is assigned to the final fat-muscle boundary row position required for the fat depth measurement. If the desired strip is not found, the final fat-muscle boundary position is assigned to the average fat-muscle boundary. Once the required rib-muscle and fat-muscle boundary positions are determined, the next step calculates the loin eye muscle depth based on the two boundary positions. An accuracy flag may also be assigned to indicate measurement accuracy. The loin eye muscle depth is the difference between the two boundaries corresponding to fat-muscle (determined in fat depth automation algorithm) and rib-muscle from the previous step. This difference is divided by the pixel to mm conversion ratio (e.g., 1 mm to 3.94 pixels) for the particular setup. For example, the final loin depth formula is: Loin eye muscle depth=((Fat-muscle boundary row−rib-muscle boundary row)/3.94)*1.025974.

In some cases, incorrect measurement for the loin eye muscle depth may result, for example, due to high contrast, dark images, high echoes, unclear or deep down ribs, and blur that may cause false decisions on rib column position, rib top boundary row, and fine adjustment of rib-muscle boundary. Hence, an accuracy flag may be assigned to each measurement to indicate a confidence level. The flag may be assigned to '0' for correct and '1' for incorrect (or high probability of incorrect) measurement. This flag may be set to 1 based on the image characteristics encountered across the algorithm and are listed below:

i) Rib1=0 and/or Rib2=0
ii) Rib-muscle boundary=0
iii) Rib-muscle boundary ≧420 (i.e., last allowable line)
iv) (Rib1-Rib2)>200 (i.e., largest allowable difference)

v) (Rib1 top-Rib2 top)≧40 (i.e., largest allowable difference)

vi) image histogram mean <45

The fat depth and loin eye muscle depth may be used to predict the percentage of fat-free lean in pork muscle tissue. The National Pork Producers Council has published six different equations for predicting fat-free lean based on the fat and muscle depth measurement system (NPPC, 2001). The equation given below calculates the percent fat-free lean based on the ultrasound fat and loin depth measurements.

Perc_lean=((15.31+(0.51*hot carcass weight)+
(((3.813*loin depth)−(31.277*fat depth))/25.4))/
hot carcass weight)*100

Table 1 presents the results of automation of backfat depth and loin eye muscle thickness measurements based on scanning 504 live animals. The images were collected using the Sensoray frame grabber and two ultrasound scanners—Aloka SSD 500V and Aquila Vet. Auto depth measurements were compared with the manual measurements done by a certified and experienced technician. The accuracy statistic for fat and loin depths is defined as an absolute difference of less than 3 mm between auto and manual measurements.

TABLE 1

Comparison results for auto and manual measurements for fat and loin depth for live pigs.

|  | Aloka SSD 500V | Aquila Vet |
| --- | --- | --- |
| Total pigs scanned | 504 | 504 |
| Fat depth accuracy | 96.63% | 95.44% |
| Loin depth accuracy | 97.03% | 96.43% |

Table 2 presents the results of automation of backfat depth and loin eye muscle thickness measurements on swine carcasses. The images were collected using the Sensoray frame grabber and Aloka SSD 500V ultrasound scanner for 749 carcasses at a line speed of 1200 carcasses per hour. Auto depth measurements were compared with the manual measurements done by a certified and experienced technician. The accuracy statistic for fat depth comparison is defined as an absolute difference of less than 3 mm between auto and manual measurements. The accuracy statistic for loin depth is defined as an absolute difference of less than 6 mm between auto and manual measurements.

TABLE 2

Comparison results for auto and manual measurements for fat and loin depth for swine carcasses.

|  | Accuracy (%) | Standard error of prediction |
| --- | --- | --- |
| Total carcasses scanned | 749 | 749 |
| Fat depth | 96.03% | 1.47 |
| Loin depth | 96.65% | 3.77 |
| Percent Lean | N/A | 0.96 |

The number and diversity of the various embodiments show the surprising versatility and effectiveness of the devices and methods associated with embodiments of the present invention. For instance, the surprising effectiveness and accuracy of the developed image processing algorithms facilitates usage in a variety of applications and environments. In another instance, the flexibility to apply filters to the data and algorithms provides a surprisingly robust and efficient solution to a number of different problems. Thus, the embodiments disclosed herein should not be viewed as limiting and should be recognized as providing support for a variety of variations and related applications.

One such application relates to a method of assessing tissue characteristics or attributes in a portion of muscle tissue. The method includes selecting a region of interest within an image of the portion of muscle tissue; applying image texture processing to the region of interest; and extracting, responsive to the image texture processing, tissue characteristics or attributes of the portion of muscle tissue. The step of selecting a region of interest within an image of the portion of muscle tissue can include the use of fat and loin depth measurements and/or rib boundaries. In some instances, a set of texture parameters derived from images of the portion of muscle tissue can be used in combination with a prediction formula.

Other applications relate to one or more of the following. Regression modeling, statistical editing or pass filter can be used in accordance with any embodiments of the present invention. Images can be filtered based upon one or more of pressure sensing, histogram thresholding, grey-scale gating, reflection intensities, blurriness, contrast levels, undesirable echo artifacts, and electromagnetic interference. Systems, algorithms or parameters can be normalized across a variety of devices and components. Automated positioning systems can be used for placement of an image probe/sensor on a portion of muscle tissue in accordance with a variety of embodiments. Different portions of muscle tissue can be sorted as a function of determined characteristics for portions of muscle tissue. The devices, methods, systems or arrangements of various embodiments of the invention can be applied to live animals, which can be useful for determining animal yield and quality calculations for the animals.

Aspects of the present invention lend themselves to implementations in a variety of devices including, but not limited to, hardware circuitry, programmable logic devices, firmware, software, and combinations thereof. A specific example includes computer readable medium storing computer executable instructions that when executed by a processor perform one or more of the process steps. The implementations of the various algorithms and methods described herein effectively transforms what would otherwise be a general purpose processor into a specially-programmed processor that is configured and arranged to implement the specialized algorithms.

It should be apparent that the various methods and algorithms discussed herein represent more than abstract concepts and mental steps. For instance, embodiments of the present invention relate to the transformation of specific image-based content and include hardware interfaces with various input and output devices.

While the present invention has been described in the above description and in the claims that follow, those skilled in the art will recognize that changes may be made thereto without departing from the spirit and scope of the present invention. Such changes may include, for example, the implementation of one or more approaches including those approaches as described in the contemplated claims below which further characterize aspects of the present invention.

What is claimed is:

1. An automated method of determining subcutaneous fat depth and muscle depth in a portion of a food animal, comprising:

presenting a probe to the portion of the food animal, the probe producing a response-provoking signal;

sensing pressure exerted between the probe and the food animal portion;

determining, in response to the response-provoking signal and the sensed pressure, a skin-fat boundary, a fat-muscle boundary, and a rib-muscle boundary; and calculating the fat depth and muscle depth from the determined boundaries.

2. A method of claim 1, further including the steps of generating a plurality of images from the response-provoking signal;

executing an algorithm to discard a subset of the plurality of images in response to an indicia of image quality; and using un-discarded images from the plurality of images in the steps of determining and calculating.

3. A method of claim 1, wherein the food animal portion is a longissimus dorsi muscle of a hot carcass.

4. A method of claim 1, further including the step of using the fat depth and muscle depth to perform at least one of the following: select livestock for breeding, and rate the portion based on quality criteria, to sort livestock, and wherein the aforementioned steps are used to calibrate equipment used in performing the method.

5. A method of claim 1, further including repeating the steps of presenting, determining and calculating on subsequently processed food animal portions, wherein the steps of repeating, presenting and measuring are implemented automatically and without human intervention.

6. A method of claim 1, wherein the step of determining the skin-fat boundary, the fat-muscle boundary, and the rib-muscle boundary includes capturing at least one image representing responses of the response-provoking signal as a function of depth in the animal portion, and analyzing the captured image.

7. A method of claim 6, wherein the step of determining includes normalizing an intensity sum for each row across all columns of the image, comparing the normalized intensity sum with a predefined threshold and with a change in slope criteria, based upon the comparison of the normalized intensity sum, identifying a top interface of fat depth, and correlating the identified top interface to the skin-fat boundary.

8. A method of claim 6, wherein the step of determining includes the steps of calculating a grey level intensity histogram mean for selected moving horizontal image stripes, comparing the calculated grey level intensity histogram mean with a predefined threshold, and based upon the comparison, identifying interfaces within the captured image that correspond to fat layers.

9. An automated method of determining subcutaneous fat depth and muscle depth in a portion of a food animal, comprising:

presenting a probe to the portion of the food animal, the probe producing a response-provoking signal;

determining, in response to the response provoking signal, a skin-fat boundary, a fat-muscle boundary, and a rib-muscle boundary;

calculating the fat depth and muscle depth from the determined boundaries wherein the step of determining the skin-fat boundary, the fat-muscle boundary, and the rib-muscle boundary includes capturing an image representing responses of the response-provoking signal as a function of depth in the animal portion, and analyzing the captured image and wherein the step of analyzing the captured image further includes the steps of calculating intensity average values for vertical stripes moving across a width of the captured image below the fat-muscle boundary, comparing the calculated intensity average values for the vertical stripes, and based upon the comparison, identifying rib shadow column locations.

10. A method of claim 9, further including the steps of calculating intensity average values for small horizontal stripes across each identified rib shadow column location, comparing the calculated intensity average values for small horizontal stripes, and based upon the comparison of the calculated intensity average values for small horizontal stripes, identifying rib top boundaries.

11. A method of claim 10, wherein the step of determining the rib-muscle boundary further includes the step of comparing intensity average differences for a pair of consecutive horizontal stripes between a pair of identified rib column locations.

12. A system for measuring the subcutaneous fat depth and muscle depth in a portion of muscle tissue in a food animal, the system comprising:

a probe configured and arranged to carry a response-provoking signal to the portion of muscle tissue; and a data processor configured and arranged to automatically generate a plurality of images from the response-provoking signal;

select a subset of a plurality of images in response to an indicia of image quality;

determine a skin-fat boundary, a fat-muscle boundary, and a rib-muscle boundary as a function of the response-provoking signal and the selected subset of images, and to calculate the fat depth and muscle depth from the determined boundaries.

13. The systems of claim 12, further comprising a pressure sensor for sensing pressure being exerted between the probe and the food animal.

14. A device assessing the subcutaneous fat depth and muscle depth of a portion of muscle tissue from a food animal, comprising:

an image sensor configured and arranged to image the portion of muscle tissue;

pressure sensors configured and arranged to detect pressure exerted between the food animal and the image sensor;

an image processor configured and arranged for generating image parameters from images obtained from the image sensor and for generating an assessment of the subcutaneous fat depth and muscle depth of the portion of muscle tissue; and a user interface configured and arranged to allow human interaction with the device.

15. The device of claim 14, wherein the image sensor is an ultrasound imaging probe having indicators that alert an operator of the current amount of pressure being detected.

16. A non-transitory computer readable medium comprising: computer executable instructions adapted to perform the steps of:

in response to a probe presented to a food animal and producing a response-provoking signal to muscle tissue from the food animal;

generating a plurality of images from the response-provoking signal;

selecting a subset of a plurality of images in response to an indicia of image quality;

determining, in response to the response-provoking signal and the selected subset of images, a skin-fat boundary, a fat-muscle boundary, and a rib-muscle boundary; and calculating the fat depth and muscle depth from the determined boundaries.

17. The method of claim 1, wherein the step of determining includes identifying rib shadow column locations.

18. The method of claim 1, further including a step of identifying a region of interest by identifying rib shadow column locations and wherein the region of interest is used in the step of determining.

19. The method of claim 1, further including a step of identifying rib top boundaries for intensity average values of horizontal stripes.

20. The method of claim 1, wherein the step of determining the rib-muscle boundary further includes a step of comparing intensity average differences for a pair of consecutive horizontal stripes between a pair of rib column locations.

21. The method of claim 1, wherein the automated method is carried out at line speeds of at least 1,000 carcasses per hour.

22. The method of claim 1, further including the step of acquiring, automatically, without human intervention, and in response to the response-provoking signal and the sensed pressure, a set of acceptable images.

23. The method of claim 11, wherein the data processor is further configured and arranged to automatically determine the skin-fat boundary, the fat-muscle boundary, and the rib-muscle boundary using upon statistical filtering.

* * * * *